United States Patent
Gopinathan et al.

(10) Patent No.: US 7,112,175 B2
(45) Date of Patent: Sep. 26, 2006

(54) TELE-DIAGNOSTIC DEVICE

(75) Inventors: Govindan Gopinathan, Oradell, NJ (US); Arthur R. Tilford, Yorba Linda, CA (US)

(73) Assignee: Ineedmd.com, Great Neck, NY (US)

( * ) Notice: Subject to any disclaimer, the term of this patent is extended or adjusted under 35 U.S.C. 154(b) by 0 days.

(21) Appl. No.: 10/024,105

(22) Filed: Dec. 18, 2001

(65) Prior Publication Data

US 2002/0045805 A1    Apr. 18, 2002

Related U.S. Application Data

(63) Continuation-in-part of application No. 09/884,371, filed on Jun. 19, 2001, now Pat. No. 6,595,918, and a continuation-in-part of application No. 09/741,283, filed on Dec. 19, 2000, and a continuation of application No. 09/188,971, filed on Nov. 10, 1998, now Pat. No. 6,248,064, which is a continuation of application No. 09/084,647, filed on May 26, 1998, now Pat. No. 6,224,548.

(51) Int. Cl.
    A61B 5/02      (2006.01)
    A61B 5/0205    (2006.01)
    A61B 5/024     (2006.01)
    A61B 5/0402    (2006.01)
    A61B 95/01     (2006.01)

(52) U.S. Cl. ............... 600/508; 600/300; 600/485; 600/500; 600/549; 600/561; 600/309

(58) Field of Classification Search ............... 600/300, 600/301, 386–390, 393, 508
    See application file for complete search history.

(56) References Cited

U.S. PATENT DOCUMENTS

| | | |
|---|---|---|
| 206,474 A | 7/1878 | Morel |
| 3,888,240 A | 6/1975 | Reinhold, Jr. et al. |
| 4,016,868 A | 4/1977 | Allison |
| 4,230,127 A | 10/1980 | Larson |
| 4,381,012 A | 4/1983 | Russek |
| 4,510,939 A | 4/1985 | Brenman et al. |
| 4,583,547 A | 4/1986 | Granek et al. |
| 4,608,987 A | 9/1986 | Mills |
| 4,662,378 A | 5/1987 | Thomis |

(Continued)

FOREIGN PATENT DOCUMENTS

EP    0 459 239 A2    12/1991

*Primary Examiner*—Robert L. Nasser
(74) *Attorney, Agent, or Firm*—Brooks Kushman P.C.

(57) ABSTRACT

A system (10), probe, and method for collecting a plurality of diagnostic information and transmitting the diagnostic information to a remote location. The system (10) comprises a member (12) contoured to at least a portion of a person's hand, and an interface unit (20) in electrical communication with the member (12). The interface unit (20) is capable of transmitting information to a remote location. The member (12) comprises at least eight sensors.

26 Claims, 4 Drawing Sheets

U.S. PATENT DOCUMENTS

| | | |
|---|---|---|
| 4,698,848 A | 10/1987 | Buckley |
| 4,709,704 A | 12/1987 | Lukasiewicz |
| 4,974,607 A | 12/1990 | Miwa |
| 5,007,427 A | 4/1991 | Suzuki et al. |
| 5,224,479 A | 7/1993 | Sekine |
| 5,353,793 A | 10/1994 | Bornn |
| 5,431,170 A | 7/1995 | Mathews |
| 5,442,729 A | 8/1995 | Kramer et al. |
| 5,465,727 A | 11/1995 | Reinhold, Jr. |
| 5,511,546 A | 4/1996 | Hon |
| 5,626,151 A | 5/1997 | Linden |
| 5,640,953 A | 6/1997 | Bishop et al. |
| 5,666,404 A | 9/1997 | Ciccotelli et al. |
| 5,670,944 A | 9/1997 | Myllymaki |
| 5,687,738 A | 11/1997 | Shapiro et al. |
| 5,704,364 A | 1/1998 | Saltzstein et al. |
| 5,730,140 A | 3/1998 | Fitch |
| 5,738,104 A | 4/1998 | Lo et al. |
| 5,771,001 A | 6/1998 | Cobb |
| 5,771,891 A | 6/1998 | Gozani |
| 5,855,550 A | 1/1999 | Lai et al. |
| 5,877,675 A | 3/1999 | Rebstock |
| 6,022,321 A | 2/2000 | Amano et al. |
| 6,217,523 B1 | 4/2001 | Amano et al. |
| 6,224,548 B1 | 5/2001 | Gopinathan et al. |
| 6,248,064 B1 | 6/2001 | Gopinathan et al. |
| 6,341,229 B1 * | 1/2002 | Akiva ........................ 600/388 |
| 6,516,289 B1 * | 2/2003 | David ........................ 600/384 |
| 6,540,673 B1 * | 4/2003 | Gopinathan et al. ........ 600/300 |
| 6,560,473 B1 * | 5/2003 | Dominguez ................. 300/382 |
| 6,589,171 B1 * | 7/2003 | Keirsbilck ................... 600/300 |
| 6,595,918 B1 * | 7/2003 | Gopinathan et al. ........ 600/300 |
| 6,611,705 B1 * | 8/2003 | Hopman et al. ............. 600/509 |

* cited by examiner

TELE-DIAGNOSTIC DEVICE

CROSS-REFERENCE TO RELATED APPLICATIONS

This application is a continuation-in-part of U.S. patent application Ser. No. 09/884,371, filed Jun. 19, 2001 now U.S. Pat. No. 6,595,918, and Ser. No. 09/741,283, filed Dec. 19, 2000. U.S. patent application Ser. No. 09/884,371 is a continuation of U.S. patent application Ser. No. 09/188,971, filed Nov. 10, 1998, now U.S. Pat. No. 6,248,064, issued on Jun. 19, 2001, which is a continuation-in-part of U.S. patent application Ser. No. 09/084,647, filed May 26, 1998, now U.S. Pat. No. 6,224,548, issued on May 1, 2001. U.S. patent application Ser. No. 09/741,283 is a continuation of U.S. patent application Ser. No. 09/084,647, filed May 26, 1998, now U.S. Pat. No. 6,224,548, issued May 1, 2001.

BACKGROUND OF THE INVENTION

1. Field of the Invention

This invention relates to a probe, and a system and method for use with the probe, for obtaining medical diagnostic and monitoring information from persons and others using the probe.

2. Background Art

Doctor-patient relationships are as old as human civilization itself. Over the centuries this relationship has undergone, surprisingly enough, very little change. One way or another the patient and the doctor came into contact with each other in person. This process was called a patient visit or doctor visit, as the case may be. From the very beginning of this patient-doctor interaction, a certain format and structure evolved and later this was laid down as a stipulated discipline in the practice of medicine. The doctor interrogates the patient in a methodical way, the patient provides the answers, which in fact, is the history of the evolution of the patient's illness. The doctor then examines the patient, makes crucial observations and gathers diagnostic data, or information, which are the fingerprints of the illness the patient is suffering from. An intellectual process ensues in the doctor's mind, where he correlates the history of the illness with the diagnostic information he gathered and the conclusion he arrives at, essentially, is the diagnosis of the patient's malady.

Over the years, innovations like the telegraph, the telephone, fax machines and of late, the e-mail and the Internet, has enhanced the patient-doctor relationship quite substantially. These innovations have curtailed the need for more frequent personal visits, by the patient or the doctor, as the case may be. Doctors on their part however, always prefer to speak to the patient and gather vital diagnostic information personally by themselves, even when the patient is located remotely from the doctor. U.S. Pat. Nos. 6,224,548 and 6,248,064, assigned to the assignee of the present application, disclose diagnostic probes and systems for collecting and transmitting diagnostic information to a remote location. The probes disclosed in those patents are capable of generating 3, 5 and 7 leadwire scenarios. While these scenarios are excellent for providing emergency diagnosis, a thorough examination, such as one that is typically conducted during a physical or routine check-up, typically calls for the generation of at least 10 leadwires so that at least an 11 lead EKG, and preferably a full conventional 12 lead EKG, can be generated.

Accordingly, it would be desirable to provide an inexpensive, simple to use, and portable probe device, system and method that could gather diagnostic/monitoring information, including at least a 10 leadwire EKG to enable generation of an 11 lead EKG, and preferably a 12 lead EKG.

SUMMARY OF THE INVENTION

An object of the present invention is to provide an inexpensive, simple to use, and portable probe, and a system and method for use with the probe, that could gather a plurality of diagnostic/monitoring information, including a 10 leadwire EKG.

In carrying out the above object, a system for collecting diagnostic information and transmitting the diagnostic information to a remote location is provided. The system comprises a member contoured to at least a portion of a person's hand and an interface unit in electrical communication with the member. The interface unit is capable of transmitting information to a remote location. The member comprises at least eight sensors.

DETAILED DESCRIPTION OF THE PREFERRED EMBODIMENTS

The present invention relates to a diagnostic/monitoring probe, and a system and method for use with the probe, for obtaining medical diagnostic information. In particular, the present invention relates to a probe, and a system and method for use with the probe, for obtaining cardiac related diagnostic and monitoring information.

Figure 1:
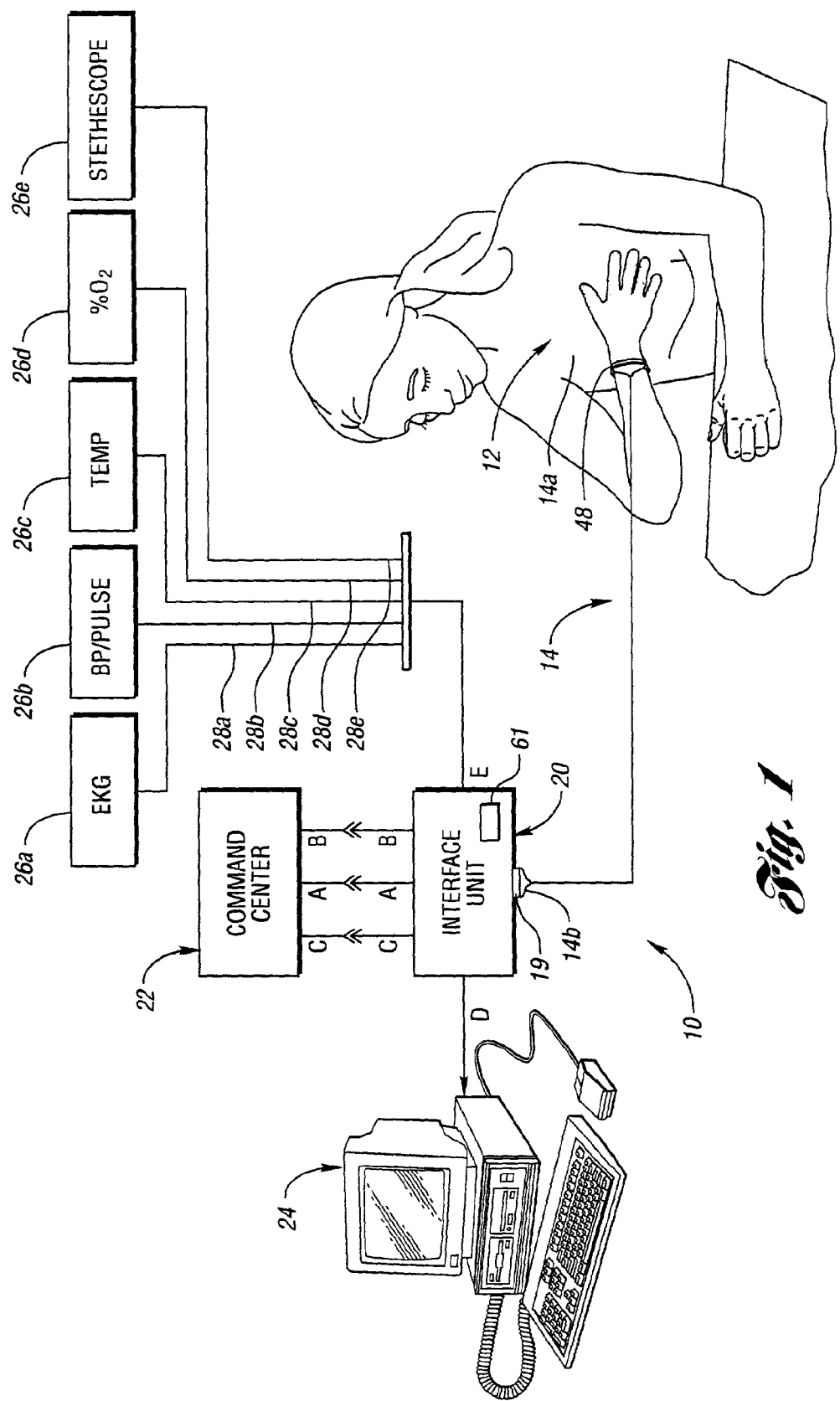
FIG. 1 is a schematic view of the system of the present invention.

As representative of the present invention, FIG. 1 illustrates a system 10 for obtaining diagnostic information. The system 10 includes a glove probe 12. The glove probe 12 is a unitary member which is adaptable to be worn over a person's hand. The glove probe 12 includes a plurality of medical diagnostic probes which detect diagnostic signals, as will be explained in more detail below. The glove probe 12 is preferably connected via a cable 14 to an interface unit 20 and, thus communicates with, and is capable of transmitting diagnostic signals, or information, from the medical diagnostic probes to the interface unit. The glove 12 could alternatively be in wireless communication such as IR or RF, with the interface unit 20. The interface unit 20 can communicate with a remote command center 22 via a telephone wire or fiber A, a satellite connection B, or a radio wave (wireless) connection C. The interface unit 20 alternatively can communicate with a personal computer (PC) 24 via an interface connection D. The interface unit 20 can also communicate with a plurality of local diagnostic readout apparatuses 26a, 26b, 26c, 26d, and 26e via EKG interface connections E and 28a, 28b, 28c, 28d and 28e, respectively, or the like. The diagnostic readout apparatuses 26a–e are preferably an electrocardiogram (EKG) readout, a blood pressure (BP) and pulse readout, a temperature readout, an % $O_2$ oxygen readout, and a stethoscope, respectively.

Figure 2:
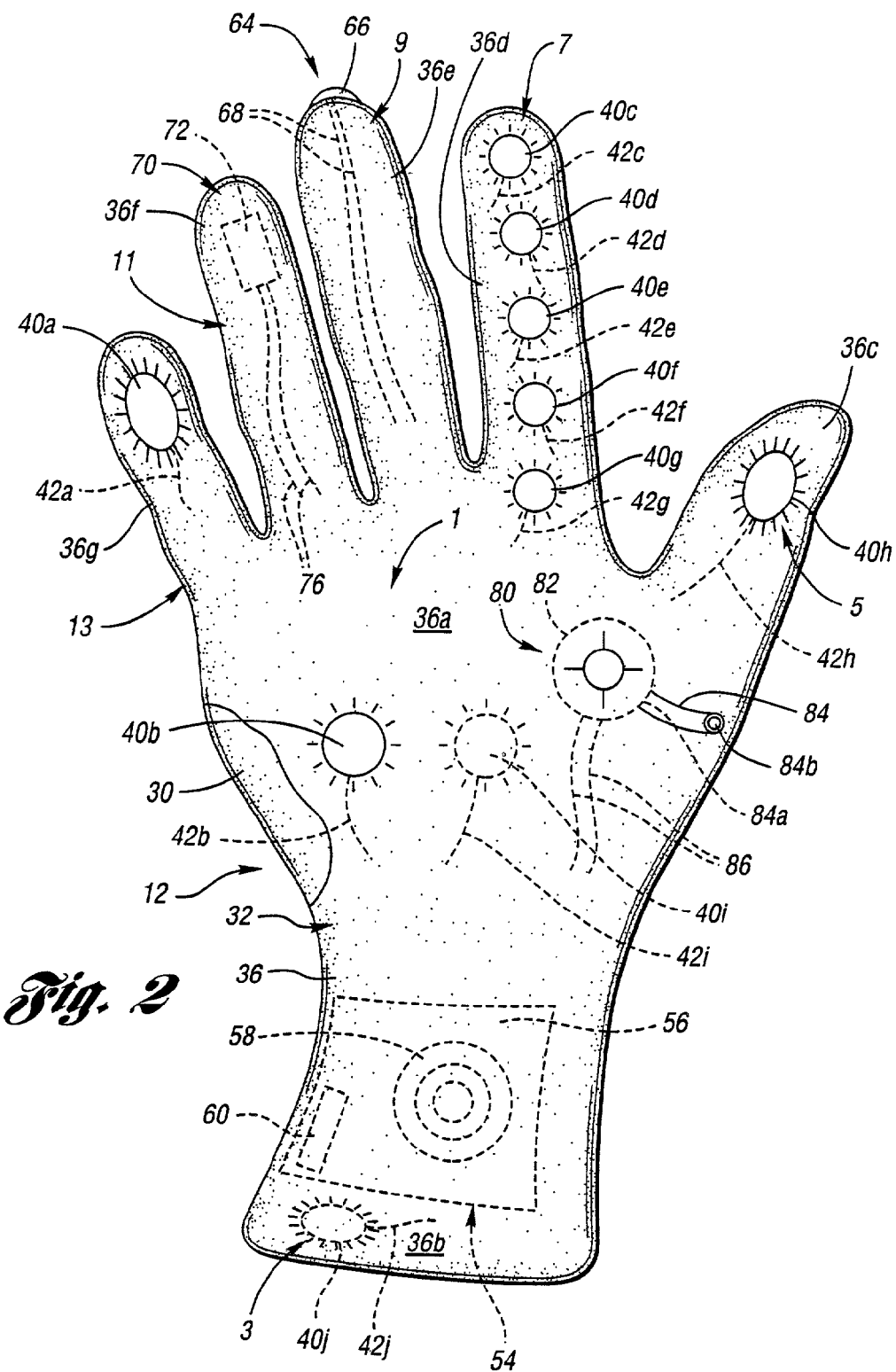
FIG. 2 is a plan view of a first, palmar, side of an apparatus of the present invention.

Referring to FIG. 2, the glove probe 12 comprises a first glove layer 30 and a second glove layer 32 secured to the first glove layer such that the second glove layer overlies at least most, and preferably all, of the first glove layer. The first glove layer 30 is preferably made of a cloth of natural or synthetic fibers, leather, or other suitable material. The second layer 32 is preferably made of a rubber or rubber-like material, such as Nitrile.

Figure 3:
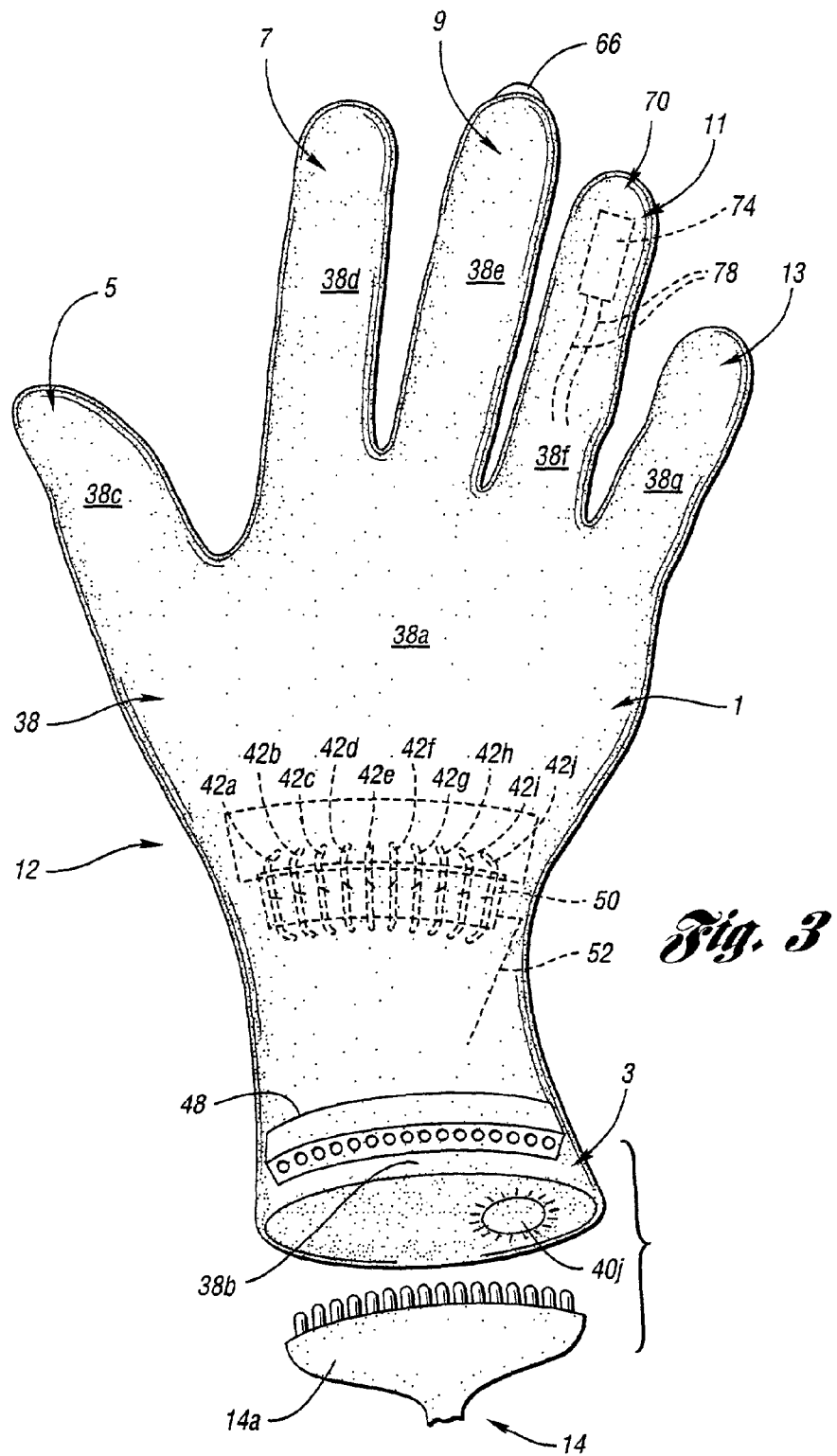
FIG. 3 is a plan view of a second, dorsal, side of an apparatus of the present invention.

The glove probe 12, which has portions shaped to the contour of a person's hand, includes a palm portion 1, a wrist portion 3, a thumb phalange portion 5, an index finger phalange portion 7, a middle finger phalange portion 9, a ring finger phalange portion 11 and a pinky finger phalange portion 13. The glove probe 12 further includes a palmar side 36 (FIG. 2) and a dorsal side 38 (FIG. 3). The palmar side 36 (FIG. 2) includes a palmar palm portion surface 36a, a palmar wrist portion surface 36b, a palmar thumb phalange portion surface 36c, a palmar index finger phalange portion surface 36d, a palmar middle finger phalange portion surface 36e, a palmar ring finger phalange portion surface 36f and a palmar pinky finger phalange portion surface 36g. The dorsal side 38 (FIG. 3) includes a dorsal palm portion surface 38a, a dorsal wrist portion surface 38b, a dorsal thumb phalange portion surface 38c, a dorsal index finger phalange portion surface 38d, a dorsal middle finger phalange portion surface 38e, a dorsal ring finger phalange portion surface 38f and a dorsal pinky finger phalange portion surface 38g.

As discussed previously, the glove probe 12 contains a plurality of medical diagnostic/monitoring probes. In the embodiment shown in FIGS. 2 and 3, the glove probe 12 contains an EKG diagnostic device, a blood pressure and pulse rate device 54, a temperature device 64, a % $O_2$ device 70, and an auscultation device 80.

The EKG device is capable of measuring the EKG currents of the heart muscle and preferably includes a plurality of sensors 40a (FIG. 2), 40b, 40c, 40d, 40e, 40f, 40g, 40h, 40i, and 40j which are secured to the first layer 30 of the glove probe 12. Exemplary sensors are described in detail in U.S. patent application Ser. No. 09/971,204, entitled "Sensor Electrode" filed on Oct. 4, 2001. In general, each of the sensors 40a–40j includes a stainless-steel mesh screen on top of a mesh or coiled cylindrical wall and an EKG jelly sponge disposed within the cylindrical wall between the screen and, preferably, the first glove layer 30 of the glove probe 12. Sensors 40a–40j are all mounted on the palmer side 36 of the glove probe 12. Each of the sensors 40a–40h preferably extends through, or are not covered by, the second glove layer 32 so that they are exposed to the environment, allowing free and close contact with the skin surface of the person using the probe 12. Sensors 40i and 40j are not exposed to the environment and instead face the dorsal side 38 of the glove probe 12.

More specifically, sensor 40a (FIG. 2) is positioned on the tip portion of the palmar pinky finger phalange portion surface 36g of the glove probe 12. Sensor 40b is positioned on the left side of the palmar palm portion surface 36a in the hypothenar area/region of the glove probe 12. Sensor 40c is positioned on the tip of the palmar index finger phalange portion surface 36d of the glove probe 12. Sensor 40d is positioned directly, about 0.5 cm, below sensor 40c on the proximal upper portion of the palmar index finger phalange portion surface 36d of the glove probe 12. In other words, sensor 40d is positioned directly above the mid point on the palmar side 36 of the index finger phalange portion 7 of the glove probe. Sensor 40e is positioned directly below sensor 40d on the lower portion, directly below the mid point, of the palmar index finger phalange portion surface 36d of the glove probe 12. Sensor 40f is positioned directly below sensor 40e on the palmar index finger phalange portion surface 36d of the glove probe 12. Sensor 40g is positioned approximately directly below sensor 40f on the right side of the palmar palm portion surface 36a of the glove probe 12. Sensor 40h is positioned on the upper portion of the palmar thumb phalange portion surface 36c of the glove probe 12. Sensor 40i is positioned on the middle portion of the palmar palm portion surface 36a of the glove probe 12. Sensor 40j is positioned on the palmar wrist portion surface 36b of the glove probe 12. Both sensor 40i and 40j face the dorsal side 38 of the glove probe 12 so that they can contact a person's hand when the glove probe 12 is worn by a person. Sensors 40i and 40j could alternatively be positioned on the dorsal side 38 of the glove probe 12, on the dorsal palm portion surface 38a and the dorsal wrist portion surface 38b, respectively, and facing away from the palmar side 36 of the glove probe and activated by placing the patient's free hand over the dorsal side of the glove probe.

Each of the sensors 40a–40j is connected to a wire 42a–42j, respectively, which extends between and electrically connects a respective one of the sensors 40a–40j with a female connection plug 48 (FIG. 3), which is preferably provided on the dorsal side 38 of the glove probe 12. Each wire 42a–42j is preferably disposed between the first and second layers 30 and 32 of the glove probe 12, and is preferably secured to the first layer 30. Each wire 42a–42j may preferably be shielded and provided with a powdered-iron bead disposed adjacent to its respective sensors 40a–40j to help prevent the detection of unwanted noise.

The glove probe 12 includes a ground strip 50 which is preferably positioned on the palm portion 1 of the dorsal side 38 between the first and second layers 30 and 32. Each wire 42a–42j is connected to the ground strip 50, preferably, via each respective wire shield. The ground strip 50 is connected to a wire 52, which extends between and connects the ground strip 50 to the female connection plug 48. The ground strip 50 functions to bring existing electromagnetic forces (EMF) noise to a single electrical voltage point for removal.

The blood pressure device 54 (FIG. 2), which is capable of measuring systolic and diastolic blood pressure and pulse rate signals, is preferably secured to the first layer 30 of the glove probe 12 between the first layer and the second layer 32 on the wrist portion 3 of the palmar side 36 of the glove probe. The blood pressure device 54 preferably includes an expandable air bladder 56 defining a chamber for accommodating air or another suitable inflation fluid, an acoustical coupler 58 in the chamber and an air tube 60. The air tube 60 extends between and provides fluid and audio communication between the chamber of the air bladder 56 and the female connection plug 48. The acoustical coupler 58 is capable of collecting the sound waves in the air bladder 56 and directing the sound waves towards, and through, the air tube 60. The blood pressure device 54 is preferably made of parts similar, or identical, to parts of the UB-302 Systolic/Diastolic (Pulse) Digital Blood Pressure monitor from A+D Engineering Inc., of Milpitas, Calif. or the CWO1 wrist mounted blood pressure cuff made by Amron.

The temperature device 64 is capable of measuring temperature signals and preferably includes a thermistor 66. The thermistor 66 is preferably positioned on the tip of the middle finger phalange portion 9. The thermistor 66 is preferably secured to the first layer 30 and extends through the second layer 32. The temperature device 64 includes a pair of wires 68 which extend between and electrically connect the thermistor 66 and the female connection plug 48. The temperature device 64 is preferably made of parts similar, or identical, to parts of the Cole-Parmer E-08402-00 thermometer and Generic thermistor E-08459-10 from Cole-Parmer Instrument Company of Vernon Hills, Ill.

The % $O_2$ device 70 is capable of measuring the percent oxygen saturation in the blood (% $O_2$) signals and preferably includes a red (600–660 nm) and infra-red (880–1000 nm) LED emitter 72 and an LED (600–1000 nm) sensor 74 (FIG. 3). The LED emitter 72 (FIG. 2) is preferably secured to the inner surface of the first layer 30 on the palmar side 36 of ring finger phalange portion 11 of the glove probe 12 and the LED sensor 74 (FIG. 3) is preferably secured to the inner surface on the dorsal surface 38 of the ring finger phalange portion 11 of the glove probe such that the LED emitter faces the LED sensor. The LED emitter 72 is connected to a pair of wires 76 which extend between and electrically connect the LED emitter and the female connection plug 48. The LED sensor 74 is connected to a pair of wires 78 which extend between and electrically connect the LED sensor and the female connection plug 48. The % $O_2$ device 70 is preferably made of parts similar, or identical, to parts of the Nonin Onyx blood flow and oxygen % reader, model No. 8500M from Nonin Medical, Inc., of Plymouth, Minn., or the DS-100A oxymeter device made by Nellcor.

The auscultation device 80 (FIG. 2) is capable of detecting the sound waves local to the patient's heart and lungs and preferably includes an acoustical coupler and microphone 82, an air tube 84, and a pair of wires 86. The acoustical coupler and microphone 82 is preferably secured to the right side of the palm portion 1 of the palmar side 36 of the glove probe 12, preferably on the first layer 30. The acoustical coupler and microphone 82 is capable of collecting and amplifying sound waves in relative close proximity to the acoustical coupler and microphone. The air tube 84 includes a first end 84a and a second end 84b. The first end 84a of the air tube 84 is preferably connected to the acoustical coupler and microphone 82 and the second end 84b is adaptable for connection with a stethoscope. The air tube 84, thus when connected to a stethoscope, extends between and provides audio communication between the acoustical coupler and microphone 82 and the stethoscope. The pair of wires 86 extend between and electrically connect the acoustical coupler and microphone 82 and the female plug 48. The auscultation device 80 is preferably made of parts similar, or identical, to parts of the EG Company microphone 9445 from the Electrical Gold Co. Of Scottsdale, Ariz.

The glove probe 12 could be manufactured by any suitable method. In one method, the glove probe 12 is manufactured by securing, by any suitable means, the wires, sensors, and other components to a glove, preferably made of cloth, leather or other binding material (i.e., the first layer 30). It should be noted that the wires and/or sensors could be made using flexible circuit technology, such as by using a conductive printable ink. The components of the glove probe 12 that do not extend past the second layer 32 are then covered by the second layer 32 in a suitable manner, such as by spraying or dip coating. The components of the glove probe 12 that do extend past the second layer could be covered with a removable protective covering during the formation of the second layer 32 and then removed to expose these components to the environment.

The cable 14 includes a first male plug 14a (FIG. 1), which plugs into male receptors on the female connection plug 48 on the glove probe 12, and a second male plug 14b which plugs into male receptors on female connection plug 19 on the interface unit 20. The cable 14 preferably includes a plurality of electrical wires and air tubes which extend between plugs 14a and 14b to provide electrical, audio, and fluid communication between the glove probe 12 and the interface unit 20 when the male plugs 14a and 14b are plugged into their respective female connection plugs 48 and 19. It should be understood that the cable 14 could be rendered unnecessary if wireless technology were used to transfer information between the probe 12 and the interface unit 20.

The interface unit 20 (FIG. 1) includes circuitry and components for transmitting diagnostic information, via a distal data stream, from the probe 12 to the command center 22, the PC 24 or the readout apparatuses 26a–26e. While any suitable interface unit 20 can be employed, examples of suitable interface units are described in more detail in U.S. Pat. Nos. 6,224,548 and 6,248,064. Alternatively, the interface unit could be incorporated into a palm pilot or cell phone device.

The manner of operation of the system 10 will now be described. The patient places the glove probe 12 over his or her right hand so that each of the patient's fingers are received within a respective one of the phalange portions 5–13. The glove probe 12 can then preferably be tightened around the patient's wrist by any suitable means such as a velcro strap. The glove probe 12 is then connected to interface unit 20 by cable 14.

EKG Diagnostic Information

To obtain EKG diagnostic information, the palmar side 36 of the glove probe 12 is placed over the patient's chest area proximate to the patient's heart. The sensors 40a–40j are located at strategic positions on the glove probe 12, as described above, to enable ten leadwires to generate at least an eleven lead EKG when the glove probe 12 is placed over the patient's left breast as will be explained in more detail below.

With the glove probe 12 placed in a normal manner over the left breast, it is believed that at least the following leadwires are possible:

LL acting leadwire: Sensor 40a on the tip portion of the pinky finger phalange 13 is positioned under the left breast.

LA (left arm) acting leadwire: Sensor 40i on the center of the palmar portion of the glove probe 12 is positioned above the left breast at the left shoulder quadrant.

RA (right arm) acting leadwire: Sensor 40j at the wrist portion of the glove probe 12 is positioned above and into the right shoulder quadrant.

C leadwire (ground wire): Sensor 40g on the palm portion, at the root of the index finger, of the glove portion 12 is positioned at the right sternal border.

The electrodes and leadwires connecting RA, LL and LA along with the ground or C leadwire would provide all the six limb leads, I, II, III and aVR, aVL, aVF.

Pre-Cordial Leads: Electrodes and leadwires connecting 40c, 40d, 40e, 40f, 40g, and 40h would provide V1, V2, V3, V4 and V5 pre-cordial leads (V leads) directly by the placement of the glove probe 12 on the left side of the person's chest.

The lead V6 could be computed by derivation, from the vector forces oriented towards the other five V leads, allowing a 12 lead EKG to be generated.

It should also be noted that, in the event that distortion of the EKG waveform occurs due to misplacement of the glove EKG sensors 40a–40j, correction of such could be accomplished using waveform modification circuits located at the command center 22. Such waveform modification circuitry can accomplish distortion correction utilizing waveshaping techniques which filter, compare, and re-shape into readable data.

The EKG currents, or leads, detected from the sensors 40a–40j are transmitted to the female connection plug 48, and through the cable 14 to the interface unit 20 where they can be sent to the command center 22, PC 24, or to the EKG readout apparatus 26a, preferably in a digital data stream.

Figure 4:
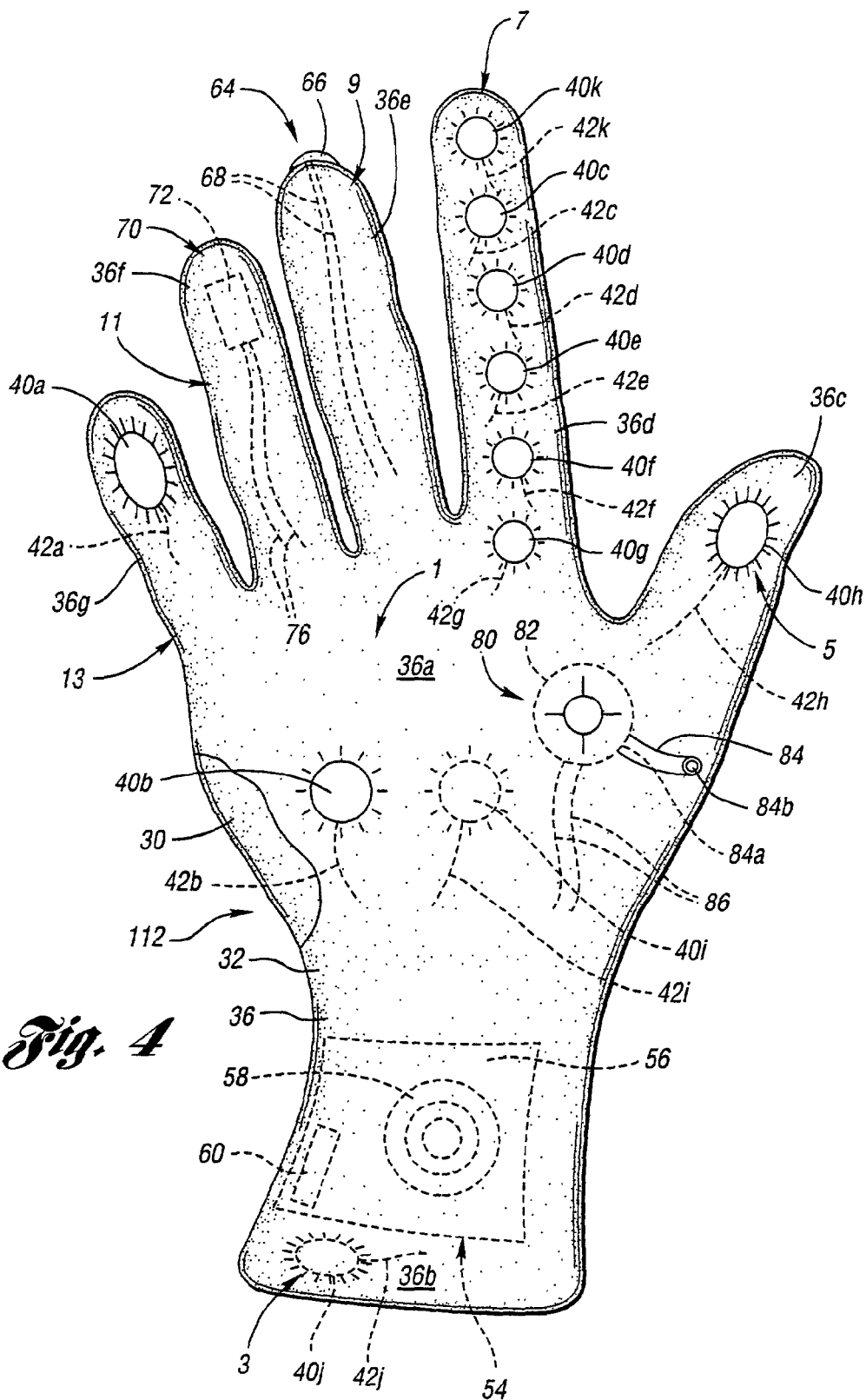
FIG. 4 illustrates another embodiment of the present invention.

In an alternative embodiment shown in FIG. 4, a glove probe 112 is provided with a somewhat longer index finger phalange portion 107 so that it is about the same length as, or as shown, longer than, the index finger phalange portion 7 of glove probe 12. Preferably, the index finger phalange portion 107 of the glove probe 112 is about 2–4 centimeters longer than the index finger phalange portion 7 of the glove probe 12 shown in FIGS. 2 and 3. In addition to sensors 40a–j, glove probe 112 further includes EKG sensor 40k disposed above sensor 40c at the tip of index finger phalange portion 107. Sensor 40k is provided to record the V6 lead directly, thereby alleviating the need to derive the V6 lead by computation/derivation from the V1–V5 leads.

Blood Pressure and Pulse Rate Diagnostic Information

To obtain blood pressure and pulse rate diagnostic information, when the glove probe 12 wrist portion 3 is tightened around the patient's wrist, the air bladder 56 is ready to accept air pressure from an associated air pump, preferably contained within the interface unit 20. The air pump then transmits inflation fluid, such as air, via the cable 14 and air tube 60, to the air bladder 56 to inflate the air bladder. Inflation of the air bladder 56 obliterates the radial artery. As the air bladder 56 releases the inflation fluid, pulse sound waves are acoustically picked-up by acoustical coupler 58 and are sent over the air tube 60 to the female connection plug 48, and through the cable 14 to the interface unit 20 where they can be sent to the command center 22, PC 24, or to the blood pressure and pulse rate readout 26b, preferably in a digital data stream, as discussed above.

Body Temperature Diagnostic Information

To obtain body temperature diagnostic information, the middle finger phalange portion 9 of the glove probe 12 is placed in an appropriate area, such as under the patient's tongue, for a period of time sufficient to receive temperature signals from the thermistor 66, preferably about one minute. The temperature signals from the temperature device 64 can be transmitted to the female connection plug 48, and through the cable 14 to the interface unit 20 where they can be sent to the command center 22, PC 24, or to the temperature readout apparatus 26c, preferably in a digital data stream.

% $O_2$ Diagnostic Information

To obtain % $O_2$ diagnostic information, the red LED emitter 72 (FIG. 2) emits red and infra-red light toward the LED sensor 74. When the light from the LED emitter 72 is passed through the patient's finger (non-painted finger nails only) at the nail, the LED sensor 74 detects the color light waves present. These signals are translated from light intensity and color quality to oxygen levels. More oxygen yields a light red blood while less oxygen produces a darker red to purple blood. It should be noted that pulse rate can also be ascertained from these readings.

The % $O_2$ signals from the % $O_2$ device 70 are then sent to the female connection plug 48, and through the cable 14 to the interface unit 20 where the % $O_2$ signals can be sent to the command center 22, PC 24, or to the % $O_2$ readout apparatus 26d, preferably in a digital data stream.

Auscultation Diagnostic Information

To listen to the heart and lungs of the patient, the glove probe 12 is moved over the patient's body to enable the acoustical coupler and microphone 82 to pick up, or hear, sound waves from the patient's heart and lungs, much like a stethoscope would. The sound waves are then transmitted to the female connection plug 48, via the pair of wires 86, and then through the cable 14 to the interface unit 20, where they can be sent to the command center or PC 24, preferably in a digital data stream as described above. Alternatively, the sound waves from the acoustical coupler of the acoustical coupler and microphone 82 could also be conducted via air tube 84 to a stethoscope 26e, as described above.

Oral Communication

To communicate orally with a remote location, such as the command center 22, a speaker/microphone 61 (FIG. 1) is provided, preferably on the interface unit 20, to transmit and receive sound waves. It should be noted that the interface unit 20 may not be able to transmit or receive sound waves via speaker/microphone 61 when processing diagnostic information from the EKG diagnostic device, the blood pressure device 54, the temperature device 64, the % $O_2$ device 70 and/or the auscultation device 80.

In an alternative embodiment, a diagnostic probe could be provided comprising a pad that contains a plurality of EKG sensors, such as ones like sensors 40a–40h and 40k, mounted on a first side of the pad and a second plurality of sensors, such as ones like sensors 40i and 40j, mounted on the other side of the pad. The pad could comprise one or more layers, preferably made of rubber or a rubber-like material, such as Nitrile. The probe could be provided with one or more handles and/or straps to allow it to be directly applied on a person's chest to enable recordation of EKG leads. The probe would be applied directly on a persons chest in substantially the same orientation as probes 12 and 112 so that the EKG sensors on the first side of the pad are placed in substantially the same orientation on a person's chest as sensors 40a–40h and 40k would be when using probes 12 and 112.

Other sensors, such as ones like sensors 40i and 40j, could be contacted by the back of the patient's hands by placing the patient's right or left hand over the back surface of the probe. The probe could be provided with suitable circuitry to enable the EKG currents or leads detected from the sensors to be transmitted to an interface unit where they can be sent to a command center, PC, or to an EKG readout apparatus in substantially the same manner as discussed above.

While the best modes for carrying out the invention have been described in detail, those familiar with the art to which the invention relates will appreciate other ways of carrying out the invention defined by the following claims. For instance, the placement of the diagnostic devices on the probes 12 and 112 and/or specific design of the diagnostic devices could vary from that described above. For instance, the EKG device could have more or fewer sensors or the sensors could be located differently than that described above. Moreover, the glove probes 12 and 112 could be adapted to be worn on the patient's left hand.

What is claimed is:

1. A system for collecting diagnostic information and transmitting the diagnostic information to a remote location, the system comprising:
   a member contoured to at least a portion of a person's hand, the member comprising at least an EKG diagnostic device, the diagnostic device comprising at least eight EKG sensors, the member comprising a palm portion, a wrist portion and a plurality of phalange portions with the EKG sensors being located on the member on at least two of the palm portion, the wrist portion, and at least one of the phalange portions; and an interface unit in electrical communication with the member, wherein the interface unit is capable of transmitting information to a remote location; wherein the plurality of phalange portions comprise an index finger phalange portion and a middle finger phalange portion, wherein the index finger phalange portion is at least as long as the middle finger phalange portion of the member.

2. The system of claim 1 wherein the EKG sensors are located on the member on the palm portion, the wrist portion and at least one of the phalange portions.

3. The system of claim 1 wherein the EKG diagnostic device comprises at least 10 sensors.

4. The system of claim 3 wherein the EKG diagnostic device comprises 11 sensors.

5. The system of claim 1 wherein the index finger phalange portion is longer than the middle finger phalange portion of the member.

6. The system of claim 1 wherein the plurality of phalange portions comprise an index finger phalange portion and a middle finger phalange portion, at least four of the EKG sensors are located on the index finger phalange portion of the member.

7. The system of claim 1 wherein at least five of the EKG sensors are located on the index finger phalange portion of the member.

8. The system of claim 1 wherein the plurality of phalange portions comprise a thumb portion, with at least one of the EKG sensors being located on the thumb portion of the member.

9. The system of claim 1 wherein the plurality of phalange portions comprise a pinky finger portion, with at least one of the EKG sensors being located on the pinky finger portion of the member.

10. The system of claim 1 wherein at least one of the EKG sensors is located on a palmer surface of the palm portion of the member.

11. The system of claim 1 wherein the member has a shape that corresponds to at least a substantial portion of a person's hand such that the member is capable of being worn on a person's hand.

12. The system of claim 11 wherein the member has a portion shaped to contour to a person's palm.

13. The system of claim 11 wherein the member has a portion shaped to contour to a person's finger.

14. The system of claim 13 wherein the member has a portion shaped to contour to a person's palm.

15. The system of claim 11 wherein the member comprises a plurality of diagnostic devices.

16. The system of claim 15 wherein the plurality of diagnostic devices includes the EKG diagnostic device, a blood pressure and pulse diagnostic device and a temperature device.

17. The system of claim 16 wherein the plurality of diagnostic devices further includes a percent $O_2$ diagnostic device.

18. The system of claim 17 wherein the plurality of diagnostic devices further includes an auscultation device.

19. The system of claim 15 wherein the plurality of diagnostic devices comprises the EKG diagnostic device, a blood pressure and pulse rate device, a temperature device, a percent $O_2$ device, and an auscultation device.

20. The system of claim 1 wherein the member comprises a glove.

21. The system of claim 1 wherein the member consists essentially of a palm portion, a wrist portion and a plurality of phalange portions.

22. The system of claim 1 wherein the wrist portion of the member is sufficiently sized that it does not extend over a substantial portion of a forearm.

23. The system of claim 1 wherein the wrist portion of the member is sufficiently sized that it extends over less than one-half of a forearm.

24. A method of obtaining and transmitting medical diagnostic information from a remote location, the method comprising:

providing a member comprising at least an EKG diagnostic device, the diagnostic device comprising at least eight EKG sensors, the member comprising a palm portion, a wrist portion and a plurality of phalange portions with the EKG sensors being located on the member on at least two of the palm portion, the wrist portion, and at least one of the phalange portions, wherein the plurality of phalange portions comprise an index finger phalange portion and a middle finger phalange portion, wherein the index finger phalange portion is at least as long as the middle finger phalange portion of the member; and using the member to collect medical diagnostic information from a first person at a remote location.

25. The method of claim 24 wherein the diagnostic information is transmitted from the first location to a second location.

26. A system for collecting diagnostic information and transmitting the diagnostic information to a remote location, the system comprising:

a member contoured to at least a portion of a person's hand, the member comprising at least an EKG diagnostic device, the diagnostic device comprising at least eight EKG sensors, the member comprising a palm portion, a wrist portion and a plurality of phalange portions with the EKG sensors being located on the member on at least two of the palm portion, the wrist portion, and at least one of the phalange portions;

wherein the plurality of phalange portions comprise an index finger phalange portion and a middle finger phalange portion, wherein the index finger phalange portion is at least as long as the middle finger phalange portion of the member.

* * * * *